Aug. 19, 1975 TAKESHI YOICHI YONEMOTO Plant Pat. 3,768
CARNATION PLANT
Filed Aug. 12, 1974
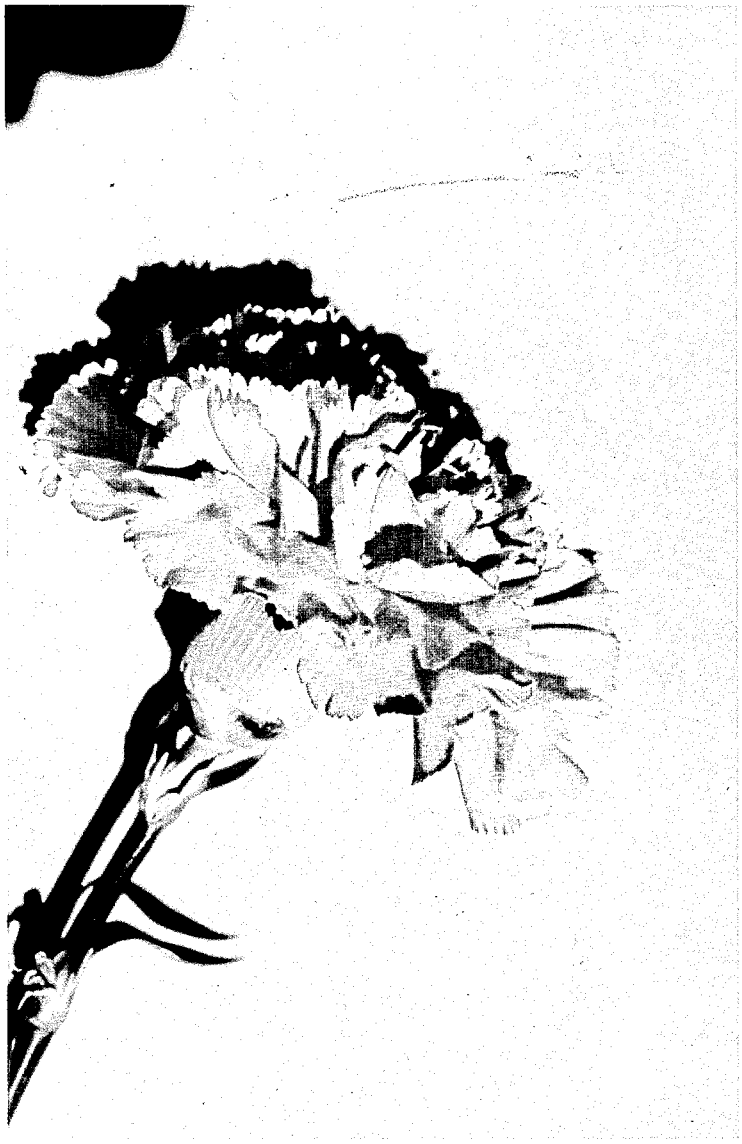

United States Patent

Plant Pat. 3,768
Patented Aug. 19, 1975

3,768
CARNATION PLANT

Takeshi Yoichi Yonemoto, 1328 Henderson Ave.,
Santa Clara, Calif. 95051

Filed Aug. 12, 1974, Ser. No. 497,128
Int. Cl. A01h 5/00
U.S. Cl. Plt.—70 1 Claim

ABSTRACT OF THE DISCLOSURE

A new variety of carnation plant of the Sim type distinguished by the very large size of its deep burnt-orange colored flowers which are borne singly on strong and sturdy stems and which bloom continuously and profusely under greenhouse culture.

*Background of the New Plant*

This new variety of carnation plant originated in my greenhouse at Santa Clara, Calif., in 1971 as a sport of the variety "Fumi" (unpatented) which in turn was a sport of "Peterson's New Pink" (unpatented). This sport was particularly noticed by me because of its deep orange blossom coloring, very much different than the two-colored yellow and red flower of its parent, and the high crown of its very large flowers. Because of the unusual and attractive color of this sport, it was asexually reproduced by me, by means of cuttings, in my greenhouse at Santa Clara, Calif., with the object of testing its worthiness for commercial propagation and propagation through successive generations has not only shown its distinctive characteristics to be firmly fixed but also has demonstrated the new plant to have a strong growth habit and to bloom profusely and continuously under greenhouse culture for cut flower production.

*Description of the Drawing*

My new variety of carnation plant is illustrated by the accompanying drawing which shows the color characteristics of a typical blossom as nearly true as it is reasonably possible to obtain by conventional photographic procedures. The true color of the blossom is shown by the color swatch mounted below the figure.

*Description of the New Plant*

The following is a detailed description of my new variety of carnation plant with the color designations according to R.H.S. Colour Chart published by The Royal Horticultural Society of London, England.

THE PLANT

Origin: Sport.
Parentage: Fumi (unpatented).
Classification:
  Botanic—*Dianthus caryophyllus.*
  Commercial—Greenhouse plant for cut flowers.
Form: Bush.
Height: Regular for Sim varieties.
Growth: Vigorous—Four months to flowering, strong and upright.

Foliage: Quantity—10 leaves per stem.
  Size of Leaf: Regular.
  Shape of Leaf: Lanceolate and curled.
  Texture: Smooth.
  Color: Green.
  Petioles: None. Leaf is amplexicaul.

THE BUD

Form: Long ovoid at time of opening.
Opening Rate: Generally 6 days. 10 days in wintertime.
Sepals: Hooded over bud until opening.
  Shape: Oval and upright.
  Color: Inside—Light Green. Outside—Green.
Calyx: Cup shaped, segments upright.
  Aspect: Smooth.
  Splitting: Small percentage split.
Peduncle: Strong and sturdy.

THE FLOWER

Blooming Characteristics: Continuous and profuse.
Size of Bloom: Very large.
  Diameter: 3 inches.
  Depth: 1½ inches.
Borne: Singly.
Shape: Cup shaped with high center. Form does not change as flower matures.
Petalage: Number of petals—70.
  Arrangement: Imbricated closely.
  Color: R.H.S. 43B some petals blotched with white. Reverse side—Coloring is lighter.
  Texture: Soft.
  Appearance: Satiny.
  Persistence: 10 days.
Fragrance: Typical carnation.
Lasting Quality: 10 days as cut flower.

REPRODUCTIVE ORGANS

Stamens:
  Anthers: Emerge from base ovary. Number—6 to 8. Size—Tiny (rudimentary).
  Filaments: Length—½ to ¾ inch. Color—White.
  Pollen: None.
Pistils: Number—3.
  Stigmas: Color—Reddish.
  Styles: Length—1 inch or more.
Ovaries: Round and segmented (½" x ½").
  Color—Green with orange tips.

Whereas the parent "Fumi" is a gold colored flower with pencil-thin red stripes, the sport of "Fumi" is a deep orange, blotched only with white and does not resemble its parent whatsoever. The color of this new variety is distinctly in its own class.

I claim:

1. The new and distinct variety of carnation plant, substantially as herein shown and described, characterized by its large orange-red blossoms and its profuse and continuous production as a greenhouse plant.

No references cited.

ROBERT E. BAGWILL, Primary Examiner